(12) United States Patent
D'Amico

(10) Patent No.: US 7,875,754 B2
(45) Date of Patent: Jan. 25, 2011

(54) METHOD OF IMPROVING ALKYLATE YIELD IN AN ALKYLATION REACTION

(75) Inventor: Vincent James D'Amico, Glen Ridge, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 1004 days.

(21) Appl. No.: 11/494,033

(22) Filed: Jul. 27, 2006

(65) Prior Publication Data
US 2008/0027263 A1     Jan. 31, 2008

(51) Int. Cl.
*C07C 2/00* (2006.01)
*C07C 2/58* (2006.01)

(52) U.S. Cl. ............... 585/301; 585/706; 585/709; 585/721; 585/722; 585/901; 585/906; 585/951

(58) Field of Classification Search .......... 585/706, 585/721, 722, 709, 901, 906, 951, 955, 316, 585/449, 301
See application file for complete search history.

(56) References Cited

U.S. PATENT DOCUMENTS

| | | | | |
|---|---|---|---|---|
| 5,304,697 A | * | 4/1994 | Peferoen et al. ......... | 585/720 |
| 5,491,277 A | * | 2/1996 | Stine et al. ............. | 585/719 |
| 5,523,503 A | * | 6/1996 | Funk et al. ............. | 585/446 |
| 5,986,158 A | * | 11/1999 | Van Broekhoven et al. . | 585/722 |
| 6,855,856 B2 | * | 2/2005 | van Broekhoven et al. .. | 585/722 |
| 2002/0198421 A1 | * | 12/2002 | Van Broekhoven et al. . | 585/446 |

FOREIGN PATENT DOCUMENTS

EP          640575 A1  *  3/1995

* cited by examiner

*Primary Examiner*—Glenn A Caldarola
*Assistant Examiner*—Bradley Etherton

(57) ABSTRACT

A method of operation for producing high yield of alkylate product using catalytic reactors. The catalytic reactors which cycle between reaction mode and catalyst regeneration mode have their contents exchanged with each other at the beginning of each cycle in order to increase the yield of the desired product. This exchange increases the yield by minimizing the contact of reactant in reaction mode with regenerant utilized in regeneration mode. Thus, reducing/preventing the undesirable alternate reaction between the two, which consumes the reactant making it unavailable for the production of the desired product.

6 Claims, 1 Drawing Sheet

METHOD OF IMPROVING ALKYLATE YIELD IN AN ALKYLATION REACTION

BACKGROUND OF THE INVENTION

1. Technical Field of Invention

The present invention relates generally to alkylation reactions. More particularly, the present invention relates to a method of improving alkylate yield in an alkylation reaction process having dual reactor schemes by exchanging the reactor contents between reaction and catalyst regeneration steps.

2. Description of Prior Art

Alkylation is a chemical process by which an alkylatable compound, such as isobutane or another similar branched saturated hydrocarbon (i.e. isoparaffin), is reacted with an alkylation agent, such as a low molecular weight olefin, in the presence of an acid catalyst to produce a higher molecular weight product. The product is an alkylate composed of a mixture of high-octane, branched-chain paraffinic hydrocarbons. Alkylate is a highly desirable gasoline blend stock because it is clean burning and has exceptional anti-knock properties.

It is known in the prior art to utilize a cyclic reactor scheme as a method of continuous operation of an acid catalyst alkylation process. A cyclic reactor scheme includes two or more reactors alternating between an alkylation reaction and catalyst regeneration. These alternating reactor schemes utilize solid acid catalysts, such as zeolite-containing catalysts. Solid acid catalysts are preferable to liquid acid (HF or $H_2SO_4$) catalysts because the latter are highly corrosive and can be toxic if accidentally released into the environment, such as via formation of gaseous hydrogen fluoride aerosols.

U.S. Pat. No. 5,986,158 to Van Broekhoven et al. illustrates a prior art alkylation process utilizing a cyclic reactor scheme. The alkylation process utilizes at least two catalytic reactors which cycle between an alkylation reaction mode and a catalyst regeneration mode. The catalyst utilized in the reactors is a solid catalytic material. The catalyst is known to promote the alkylation of isobutane with light olefin organic compounds ($C_3$-$C_5$) to produce alkylate having predominantly $C_7$-$C_9$ branched alkanes. Upon completion of the cycle times for the respective reaction and regeneration modes, the pair of reactors switch cycles, such that the regenerating reactor ceases regeneration mode and begins reaction mode and the reaction reactor ceases reaction mode and begins regeneration mode.

The Van Broekhoven patent does not, however, address the problem of a significant loss of alkylate product yield resulting from the co-mingling and reaction of alkylating reactant, such as $C_3$-$C_5$ olefins, with catalyst regenerent such as hydrogen. This co-mingling and reaction occurs at the beginning of each cycle when the reactors switch from the reaction mode to the regeneration mode and vice versa. The reactor entering its alkylation reaction step has just completed the catalyst regeneration step and still contains residual hydrogen from regeneration. As this reactor enters the alkylation reaction step, olefin addition begins and the olefins co-mingle and react with the residual hydrogen, resulting in the saturation of the olefin to its paraffinic form, for example, converting butene to butane. This lost saturated olefin is, therefore, unavailable for the alkyation reaction, resulting in the reduced yield of desired alkylate product. Similarly, a reactor entering the catalyst regeneration step still contains residual olefin from the just completed alkylation step. The olefin then mixes and reacts with the hydrogen injected during the ensuing catalyst regeneration.

These residual reactor contents for both reactors could be, for example, removed and purged to flare for disposal, transported to another holding vessel for later reprocessing, or delivered to downstream facilities where individual components can be separated, recovered, or reprocessed as appropriate. These alternatives, however, are inefficient and costly.

The prior art also includes other processes outside the field of refinery alkylation that operate cyclically and utilize a purge/displacement mode between operating steps. For example, one such process employs catalytic reactors that cycle between a reactor step, where light paraffinic hydrocarbons, such as propane and isobutene, are dehydrogenated to olefins, such as propylene and isobutene respectively, and a catalyst regeneration step, where catalyst activity is restored via the burn-off of coke residues with oxygen. Reactor purging is undertaken between these steps to prevent the undesirable reaction of hydrocarbons from the reactor step with oxygen from the regeneration step, which would result both in a product yield loss and potentially unstable reactor operating conditions caused by the resulting heat of combustion. Specifically, at the end of the reaction step and prior to the commencement of regeneration, steam is injected into the reactor to purge the contained hydrocarbons to the downstream product separation and recovery system. Similarly, at the end of catalyst regeneration step and prior to the commencement of the reaction step, hydrogen is injected into the reactors to react with the residual oxygen to form water and purge the reactors. The effluents from these purge/reaction steps are each directed to downstream processing facilities. There is no exchange of purged fluids between reactors. This results in a loss of materials and the creation of a waste stream. This method suffers from low efficiency and high cost and has not been utilized in alkylation processes.

Another process known in the art is a cyclic adsorption process that utilizes solid adsorbents such as molecular sieves for stream separation and purification. This is combined with an intermediate purge/displacement step, wherein the fluid contents of adsorbent vessels are exchanged between the cyclic steps of adsorption and desorption. Examples include processes utilized for normal paraffin/iso-paraffin separation and hydrogen purification. In the adsorption processes, however, there are no catalytic reactors or chemical reactions involved, but rather a separation of feed components, and the primary purpose of the purge/displacement exchange is to improve the separation factor and resulting purity of the recovered product(s).

A need exists for an alkylation method using a cyclic reactor scheme that results in a significant increase in the yield of alkylate product while maintaining its efficiency. A need also exists for an alkylation method that is economically and commercially viable and that minimizes capital costs associated with additional equipment.

SUMMARY OF INVENTION

The present invention advantageously provides a method of improving alkylate yield in a cyclic operating solid acid catalyst refinery alkylation process utilizing dual reactor schemes by exchanging the reactor contents between reaction and catalyst regeneration steps.

An embodiment of the present invention includes a method of operation wherein catalytic reactors cycle between alkylation reaction mode and catalyst regeneration mode and have their contents exchanged at or near the beginning of each cycle in order to increase the yield of the desired product. The method preferably minimizes the contact of reactant with regenerant, thereby reducing the likelihood of an undesirable side reaction between the two components which can consume the reactant and make it unavailable for the primary reaction which produces the desired product.

In an embodiment of the present invention, the method of improving the yield of alkylate product from a solid acid catalyst alkylation process having a first reactor and a second reactor includes the step of exchanging the liquid phase hydrogen containing contents of the first reactor with the liquid phase olefin containing contents of the second reactor prior to alkylating an amount of an alkylatable organic compound in the first reactor and regenerating an amount of spent solid acid catalyst in the second reactor.

Another embodiment of the invention includes a method of improving the yield of alkylate product from an alkylation process utilizing first and second reactors having a liquid content which includes the steps of: reacting an alkylatable organic compound with an alkylation agent in a first reactor containing a first solid acid catalyst to produce an alkylate product; contacting hydrogen dissolved in saturated hydrocarbons in a second reactor containing a second solid acid catalyst to regenerate the second solid acid catalyst; exchanging the liquid contents of the first reactor with the liquid contents of the second reactor upon regeneration of the second solid acid catalyst in the second reactor; reacting the alkylatable organic compound and the alkylation agent in the second reactor using the regenerated second solid acid catalyst to produce an alkylate product; and contacting the saturated hydrocarbons with dissolved hydrogen in the first reactor to regenerate the first solid acid catalyst in the first reactor.

A feature of one embodiment of the invention is that the method further includes the step of ceasing supply of alkylation agent to the first reactor and ceasing supply of hydrogen to the second reactor before exchanging the liquid contents of the first reactor and the second reactor.

Another embodiment of the present invention also includes a method of improving the yield of alkylate product from a solid acid catalyst alkylation process which includes the steps of: supplying an olefin feed stream and a saturated hydrocarbon feed stream to the alkylation reactor; reacting at least a portion of the olefin feed stream with at least a portion of the saturated hydrocarbon feed stream in the alkylation reactor to produce an alkylate product stream; utilizing a first portion of the alkylate product stream as an alkylation reactor recycle stream; supplying a hydrogen feed stream and a second portion of the alkylate product stream to the regeneration reactor; contacting the hydrogen stream dissolved in the second portion of the alkylate product stream with the catalyst in the regeneration reactor to produce a regeneration product stream; utilizing a portion of the regeneration product stream as a regeneration reactor recycle stream; blocking supply of olefin feed stream to the alkylation reactor; directing the alkylation reactor recycle stream from the alkylation reactor to the regeneration reactor until the residual (un-reacted) olefin in the alkylation reactor is substantially removed; blocking supply of hydrogen feed stream to the regeneration reactor; directing the regeneration recycle stream from the regeneration reactor to the alkylation reactor until the residual dissolved hydrogen in the regeneration reactor is substantially removed; resuming the supply of olefin feed stream to the former regeneration reactor (now in alkylation mode); and resuming the supply of hydrogen feed stream to the former alkylation reactor (now in regeneration mode).

The present invention advantageously results in an increase in the yield of alkylate product, a valuable gasoline blend stock, from the solid acid catalyst refinery alkylation process, thereby improving its competitiveness relative to the established liquid acid (HF and $H_2SO_4$) and other alkylation technologies.

BRIEF DESCRIPTION OF DRAWINGS

So that the manner in which the features, advantages and objectives of the invention, as well as others that will become apparent, are attained and can be understood in detail, more particular description of the invention briefly summarized above may be had by reference to the embodiments thereof that are illustrated in the drawing, which drawing forms a part of this specification. It is to be noted, however, that the appended drawing illustrates only one embodiment of the invention and is, therefore, not to be considered limiting of the invention's scope, for the invention may admit to other equally effective embodiments.

DETAILED DESCRIPTION OF DRAWINGS

Figure 1:
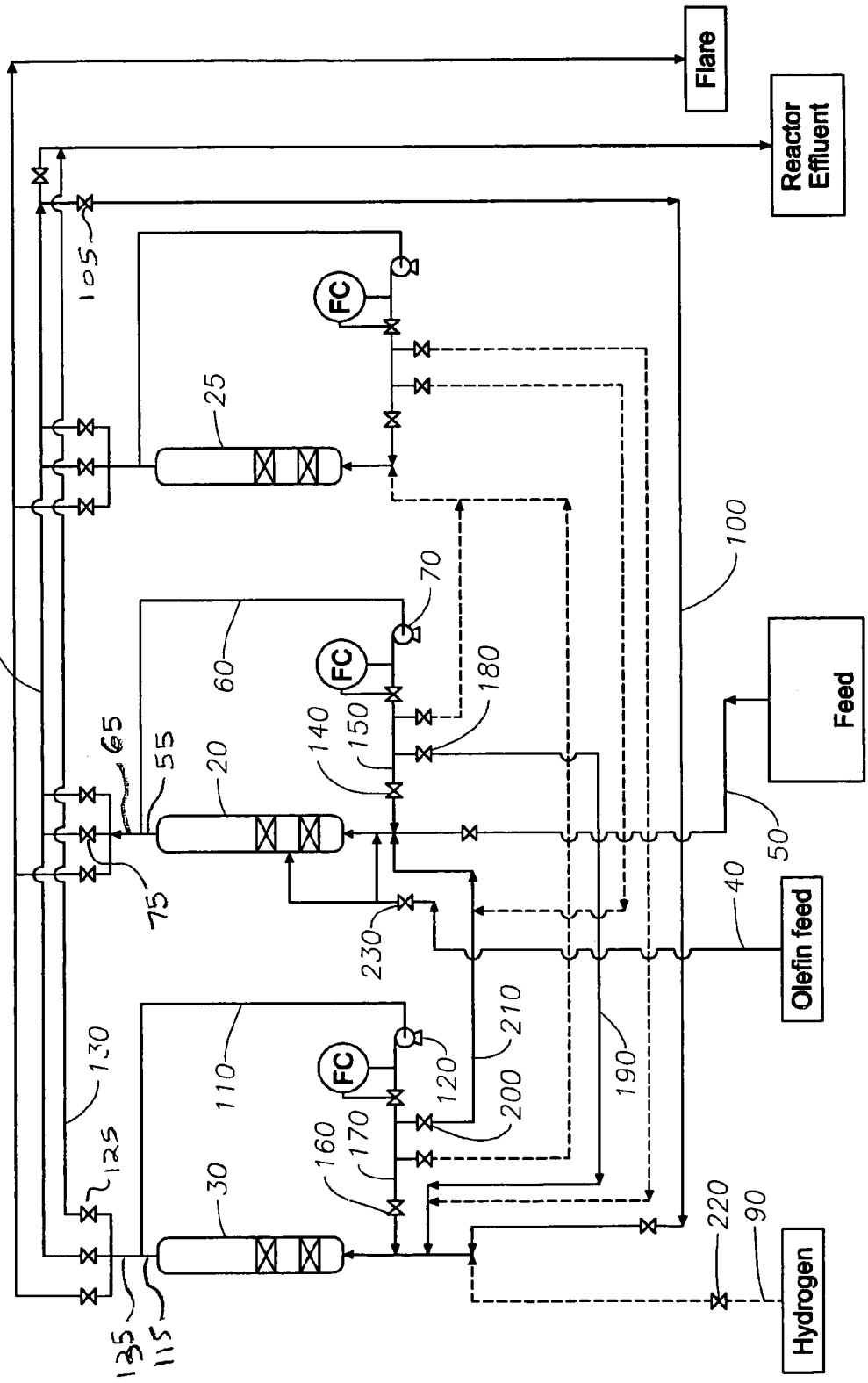
FIG. 1 is a simplified flow diagram of a process for improving alkylate yield in a cyclic operating solid acid catalyst refinery alkylation process in accordance with an embodiment of the present invention.

FIG. 1 illustrates a solid catalyst alkylation process according to an embodiment of the present invention. The catalyst is preferably a zeolite containing a noble metal component, preferably palladium or platinum. The process utilizes two or more catalytic reactors including a first reactor 20 and a second reactor 30 in cyclic mode. The first and second catalytic reactors 20, 30 contain a first solid acid catalyst and a second solid acid catalyst, respectively. One or more standby reactors 25 containing solid acid catalyst can also be utilized. The first and second catalytic reactors 20, 30 can be fixed bed type, expanded bed type, or the like, and can be comprised of one or more individual beds, preferably 2-5 beds. Operating conditions are such that the reactor contents are maintained all or substantially in the liquid phase. Operating temperature is in the range from 30° C.-100° C., preferably 50° C.-80° C., and operating pressure is in the range of 12 barg-30 barg, preferably 18 barg-24 barg.

In an embodiment of the present invention, olefin feed is introduced into first reactor 20 via stream 40 when first reactor 20 is in alkylation reaction mode. The olefin feed (alkylation agent) is preferably split between one or more reactor beds. Examples of olefins that can be utilized in the feed stream include, but are not limited to, propylene, isobutylene, n-butenes and amylenes. The olefin feed is preferably processed at an olefin weight hourly space velocity (whsv) of 0.05/hr -0.50/hr, but more preferably at 0.10/hr -0.30/hr.

An isoparaffin (alkylatable organic compound) feed is fed to first reactor 20, preferably at the inlet via stream 50, in excess to the olefin feed, such that the feed isoparaffin to olefin molar ratio (I/O) is in the range of 8-40, and preferably in the range of 16-32. Examples of isoparaffins (alkylatable organic compounds) that can be utilized include, but are not limited to, isobutane and isopentane. The olefin feed stream acts as an alkylation agent with respect to the alkylatable organic compound such that alkylation occurs within first reactor 20. At the exit of first reactor 20, flow from an exit stream 55 is preferably split, with a portion of the exit flow from stream 55 recycled to the reactor inlet via stream 60 and pump 70, and another portion of the exit flow from stream 55 providing stream 80 as alkylate product via valve 75 and stream 65. The ratio of the flow in stream 60 to the flow in stream 80 is in the range of 2-12 and preferably in the range of 4-8. The resulting overall conversion of feed olefin in the reactor 20 is at least 95%, but preferably 98% or higher.

As alkylation occurs in first reactor 20, second reactor 30 is in regeneration mode. Hydrogen feed is introduced into second reactor 30 via stream 90, first mixing with a saturated hydrocarbon, preferably the effluent from first reactor 20 in stream 80 via valve 105 and stream 100. The saturated hydrocarbon used in the regeneration process, however, can be any linear, branched or cyclic saturated hydrocarbon, or mixtures thereof, which are liquid or in the supercritical condition at regeneration temperature and pressure. For example, a portion of the alkylatable compound supplied to first reactor 20 can be used as saturated hydrocarbon in the regeneration in second reactor 30. Other examples of saturated hydrocarbons that can be utilized include, but are not limited to, n-butane and n-pentane.

The combined hydrogen/saturated hydrocarbon stream enters the second reactor 30 with the hydrogen flow rate controlled to maintain a reactor liquid phase, hydrogen molar concentration in the range of 0.5 mol %-2.0 mol %, and preferably 0.7 mol %-1.2 mol %. The contacting of the catalyst in second reactor 30 with hydrogen under these liquid phase conditions has been found to restore catalyst activity that is lost from the processing of olefin feed during the alkylation reaction mode of the reactor's previous cycle of operation. At the exit of the second reactor 30, flow in an effluent stream 115 is preferably split, with a portion of the flow in effluent stream 115 recycled to the reactor inlet via stream 110 and pump 120, and another portion of the flow in stream 115 utilized primarily as alkylate product in stream 130 via valve 125 and stream 135. The ratio of the flow in stream 110 to the flow in stream 130 is preferably operated at the same value as the ratio of flow in stream 60 to the flow in stream 80 in second reactor 20 undergoing alkylation reaction mode.

The duration or cycle time of the reaction and regeneration modes in the first and second reactors 20, 30 are preferably essentially equivalent. This cycle time can be from 15 minutes to 6 hours, preferably from 45 minutes to 2 hours. The regeneration mode is preferably carried out at 90% or less of the active cycle of the catalyst. The active cycle of the catalyst is defined as the time from the start of the feeding of the alkylation agent to the moment when 20% of the alkylation agent, relative to the concentration at the entrance of the catalyst-containing reactor section, leaves the catalyst-containing reactor section without being converted, excluding isomerisation within the molecule.

At the beginning of the cycle illustrated in FIG. 1, second reactor 30 is starting catalyst regeneration mode, and it is at least partially filled with fluid from the previous cycle, wherein it was in alkylation reaction mode. The fluid in second reactor 30 includes a remaining amount of residual liquid olefin, which had not reacted as of the end of this previous alkylation reaction mode. Liquid olefin generally means the C3-C5 olefins in the olefin feed (Stream 40). Similarly, first reactor 20 is starting alkylation reaction mode, and it is at least partially filled with fluid from the previous cycle, wherein it was in catalyst regeneration mode. The fluid in first reactor 20 includes a remaining amount of dissolved liquid hydrogen at or near the molar concentration utilized to restore catalyst activity during catalyst regeneration mode. Hydrogen is supplied in the vapor phase in line 90 and across block valve 220. It is mixed with stream 100 such that the hydrogen fully dissolves in this hydrocarbon stream and is maintained in the liquid phase in the reactor 30. Thus, either the introduction of hydrogen into second reactor 30 or olefin into first reactor 20 at the start of the cycle will cause the commingling of hydrogen and olefin in the reactors. This commingling can lead to the rapid saturation of olefin, i.e., the reaction of olefin and hydrogen to yield the corresponding (C3-C5) paraffin. This reaction is undesirable, as it consumes both valuable hydrogen and olefin, and thereby reduces the yield of the desired alkylate product.

At the beginning of each cycle, the fluid contents of the reactor starting alkylation reaction mode are preferably mutually exchanged with the fluid contents of the reactor starting catalyst regeneration mode. The first and second catalytic reactors 20, 30 preferably have all or substantially all of their liquid contents exchanged with each other at the beginning of each cycle in order to increase the yield of the desired alkylate product. This exchange minimizes the commingling of olefin, the reactant utilized in alkylation reaction mode, with hydrogen, the regenerent utilized in catalyst regeneration mode, and thereby minimizes the resulting loss of olefin via the undesirable saturation reaction.

The fluid contents of second reactor 30 and first reactor 20 are preferably simultaneously exchanged with each other at the beginning of each cycle for a period ranging from 2-10 minutes and more preferably from 4-7 minutes. This exchange is accomplished by closing both block valve 140 on stream 150 leading to first reactor 20 and block valve 160 on stream 170 leading to second reactor 30, while opening both block valve 180 on stream 190 leading to second reactor 30 and block valve 200 on stream 210 leading to first reactor 20. Thus, the fluid contents from first reactor 20 are transferred via stream 60, pump 70 and stream 190, to second reactor 30, and simultaneously, the fluid contents from second reactor 30, via stream 110, pump 120 and stream 210, are transferred to first reactor 20.

In a embodiment of the present invention, neither hydrogen nor olefin feeds are injected into second reactor 30 and first reactor 20, respectively, during this period of reactor fluid content exchange. This further reduces olefin-hydrogen commingling and is accomplished by closing both hydrogen feed block valve 220 on stream 90 to second reactor 30 and olefin feed block valve 230 on stream 40 to first reactor 20.

After the initial reactor contents exchange period, effluent from each reactor is directly pumped back or recycled to its own reactor inlet for the remainder of the cycle. Simultaneously, the flow of hydrogen for catalyst regeneration mode and olefin for alkylation reaction mode are preferably resumed to their respective reactors. This transition to the normal operating sequence is accomplished by opening block valves 160 and 220 and closing block valve 200 on second reactor 30, and opening block valves 140 and 230 and closing block valve 180 on first reactor 20.

The implementation of this inventive method of operation advantageously results in a relative increase in alkylate product yield of greater than 10% in an embodiment of the invention.

While the invention has been shown or described in only some of its forms, it should be apparent to those skilled in art that it is not so limited, but is susceptible to various changes without departing from the scope of the invention. For example, a plurality of reactors can be utilized simultaneously in the alkylation process, whereby more than one reactor can be operating in alkylation or regeneration mode at any one time.

I claim:

1. A method of producing high yield of alkylate product from an alkylation process utilizing first and second reactors having a liquid content comprising the steps of:

reacting an alkylatable organic compound with an alkylation agent in the first reactor containing a first solid acid catalyst to produce an alkylate product;

feeding a portion of said alkylate product to a second reactor;

contacting a second solid acid catalyst simultaneously with hydrogen and the fed portion of the alkylate product in the second reactor to regenerate the second solid acid catalyst;

exchanging the liquid contents of the first reactor with the liquid contents of the second reactor;

reacting the alkylatable organic compound and the alkylation agent in the second reactor using the regenerated second solid acid catalyst to produce an alkylate product; and contacting a saturated hydrocarbon and hydrogen in the first reactor to regenerate the first solid acid catalyst.

2. The method of claim 1, further comprising the step of ceasing supply of alkylation agent to the first reactor and ceasing supply of hydrogen to the second reactor before or simultaneous with exchanging the liquid contents of the first reactor and the second reactor.

3. The method of claim 1, wherein the alkylatable organic compound is selected from one or more of the group consisting of C4 isoparaffins and C5 isoparaffins.

4. The method of claim 1, wherein the alkylation agent is selected from one or more of the group consisting of C3 olefins, C4 olefins, and C5 olefins.

5. The method of claim 1, wherein the exchanging comprises simultaneously:

transferring the liquid contents of the first reactor to the second reactor; and transferring the liquid contents of the second reactor to the first reactor.

6. The method of claim 1, wherein the saturated hydrocarbon comprises alkylate product from the second reactor, the method further comprising feeding a portion of the alkylate product from the second reactor to the first reactor.

* * * * *